United States Patent [19]
Gerber

[11] Patent Number: 5,871,541
[45] Date of Patent: Feb. 16, 1999

[54] SYSTEM FOR PRODUCING A KNEE-JOINT ENDOPROSTHESIS

[75] Inventor: Bruno E. Gerber, Neuchâtel, Switzerland

[73] Assignee: Plus Endoprothetik, AG, Rotkreuz, Switzerland

[21] Appl. No.: 745,252

[22] Filed: Nov. 8, 1996

Related U.S. Application Data

[63] Continuation of Ser. No. 491,975, filed as PCT/EP94/03875 Nov. 23, 1994 published as WO95/14444 Jun. 1, 1995, abandoned.

[30] Foreign Application Priority Data

Nov. 23, 1993 [DE] Germany ........................ 43 39 895.2
Jul. 19, 1994 [DE] Germany ........................ 44 25 529.2

[51] Int. Cl.⁶ ..................................................... A61F 2/38
[52] U.S. Cl. ................................................................ 623/20
[58] Field of Search ................................ 623/20, 18, 16

[56] References Cited

U.S. PATENT DOCUMENTS

| | | | |
|---|---|---|---|
| 3,728,742 | 4/1973 | Averill et al. | 623/20 |
| 4,007,495 | 2/1977 | Frazier | 623/20 |
| 4,034,418 | 7/1977 | Jackson et al. | 623/20 |
| 4,340,978 | 7/1982 | Buechel et al. | 623/20 |
| 4,714,472 | 12/1987 | Averill et al. | 623/20 |
| 4,883,488 | 11/1989 | Bloebaum et al. | 623/20 |
| 5,047,057 | 9/1991 | Lawes | 623/20 |
| 5,395,401 | 3/1995 | Bahler | 623/20 |
| 5,470,354 | 11/1995 | Hershberger et al. | 623/20 |

FOREIGN PATENT DOCUMENTS

| | | |
|---|---|---|
| 0183670 | 6/1986 | European Pat. Off. . |
| 0021421 | 3/1988 | European Pat. Off. . |
| 0327297 | 8/1989 | European Pat. Off. . |
| 0519872 | 6/1992 | European Pat. Off. . |
| 0519873 | 6/1992 | European Pat. Off. . |
| 0498586 | 8/1992 | European Pat. Off. . |
| 2698536 | 6/1994 | France ....................... 623/20 |
| 3039992 | 5/1981 | Germany . |
| 2550704 | 6/1985 | Germany . |
| 3433264 | 10/1986 | Germany . |
| 3529894 | 8/1987 | Germany . |
| 3013155 | 9/1989 | Germany . |
| 9300791 | 7/1993 | Germany . |
| 3305237 | 2/1994 | Germany . |
| 2184025 | 6/1987 | United Kingdom . |

*Primary Examiner*—David H. Willse
*Attorney, Agent, or Firm*—Andrus, Sceales, Starke & Sawall

[57] ABSTRACT

System to produce a knee-joint endoprosthesis with joint elements (10) are constructed to be attached to the lower end of the femur, and have a convexly curved joint bearing surface. Bearing elements (12) are constructed to be attached to the upper end of the tibia (11). A meniscus (14) is movably disposed between each femoral joint element (10) and tibial bearing element (12) and are provided on its upper and lower sides with sliding surfaces complementary in shape to the associated joint bearing surface of the femoral joint element (10) and the associated bearing surface of the tibial bearing element (12), respectively. The peripheral or sagittally outer boundary (16) of the sliding surfaces (15) of the menisci (14) that face the femoral joint elements (10) is higher than their central or sagittally inner boundary. The system is designed for modular, universally compatible supplementation to form a total knee prosthesis, revision prosthesis or femoropatellar joint prosthesis.

21 Claims, 6 Drawing Sheets

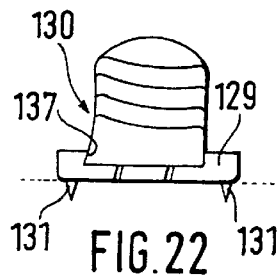
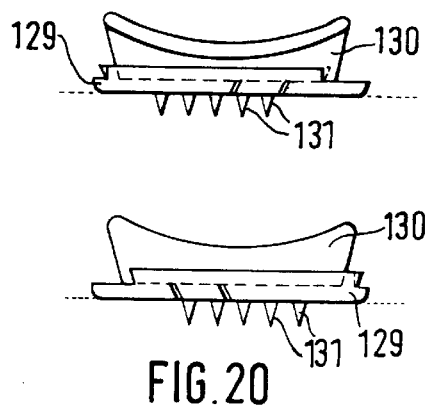
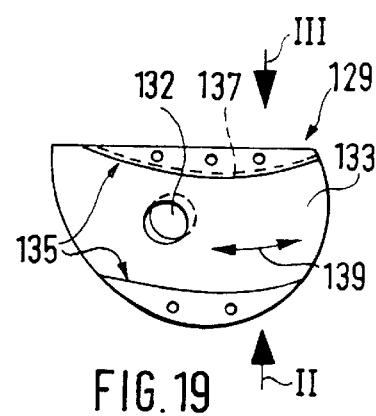
FIG.21 FIG.22 FIG.20 FIG.19
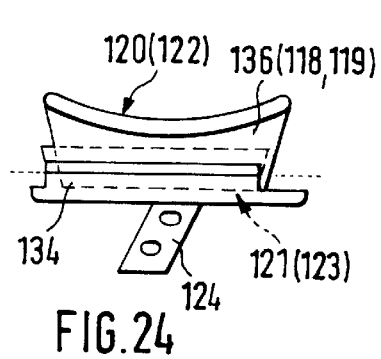
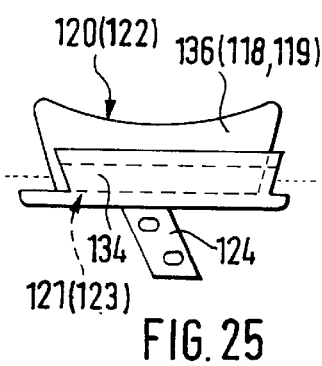
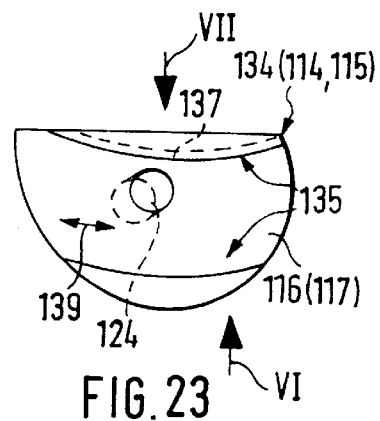
FIG.24 FIG.25 FIG.23
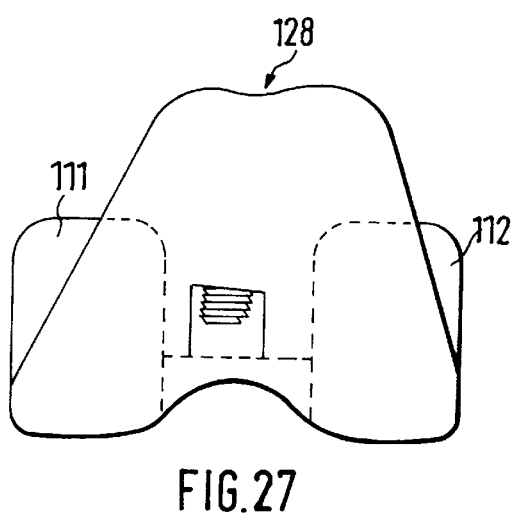
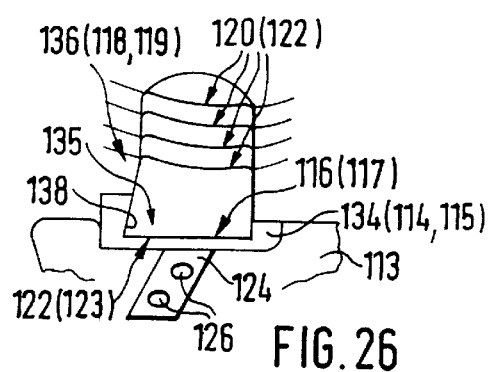
FIG.27 FIG.26

SYSTEM FOR PRODUCING A KNEE-JOINT ENDOPROSTHESIS

CROSS REFERENCE TO RELATED APPLICATION

This application is a file wrapper continuation of application Ser. No. 08/491,975, filed as PCT/EP94/03875 Nov. 23, 1994, published as WO95/14444 Jun. 1, 1995, now abandoned.

The invention relates to a system for producing a knee-joint endoprosthesis with
- joint elements having a convex joint bearing surface, which can be fixed to the lower end of the femur,
- bearing elements that can be fixed to the upper end of the tibia, and with
- a meniscus movably disposed between each femoral joint bearing element and tibial bearing element, having on its upper and lower sides sliding surfaces complementary in shape to the associated joint-bearing surface of the femoral joint element and to the associated bearing surface of the tibial bearing element, respectively.

A knee-joint endoprosthesis with the characteristics listed above is disclosed in DE 25 50 704 C2. The proposed knee-joint endoprosthesis is so constructed that to a great extent it imitates the geometry of the "natural" knee joint and its bearing surfaces. Between the joint element and the bearing element there is provided a movable meniscus element the sliding surfaces of which, arranged on the upper and lower sides, have a shape complementary to the joint bearing surface of the femoral joint element and to the bearing surface of the tibial bearing element, respectively. Such construction interferes relatively little with the natural play of the muscles and ligaments and simultaneously ensures a relatively good distribution of the load. The joint element can move relatively freely with respect to the meniscus element, as can the meniscus element with respect to the bearing element, because of the complementary shape of the opposed bearing surfaces in each pair of elements, which to some extent amount to two joint subdivisions arranged mechanically in series. In particular, the joint and meniscus elements can rotate about three orthogonal axes relative to one another, and the meniscus element and the bearing element can slide relative to one another in two of these directions and rotate with respect to one another about the third axis. The resulting capacity for movement between the joint and the bearing element thus comprises a rolling motion, a sliding motion and a rotation to provide those combinations of these forms of movement that are found in the natural knee. The substantially convex and relatively flat shapes of the two bearing surfaces can approximate so closely to the surface configuration of the natural joint parts of the associated individual knee elements that interaction with the muscles and ligaments surrounding the joint also proceeds as in the natural knee. Separate construction of both the femoral joint elements and the tibial bearing elements makes it possible to produce half-prostheses modularly adapted for assembly into a prosthesis system. In this regard the knee-joint endoprosthesis according to DE 25 50 704 C2 also differs advantageously from the knee-joint endoprosthesis according to EP 0 519 873 A2 or EP 0 519 872 A1.

It is a disadvantage of the known systems that load forces impinging on the tibia plateau in an outwardly inclined direction cannot be absorbed perpendicularly by the implant. Accordingly, it is characteristic of the known constructions that lateral stability can be ensured only by sufficiency of the natural lateral ligaments.

SUMMARY OF THE PRESENT INVENTION

Hence the primary object of the present invention is to provide a system of the kind described at the outset in which load forces that impinge on the tibia plateau in an outwardly inclined direction can be effectively absorbed by very simple means, so that the inherent stability of the knee-joint endoprosthesis in this respect is increased in comparison to the state of the art. At the same time, the above-mentioned advantages of the knee-joint endoprosthesis according to DE 25 50 704 C2 are to be retained.

This object is achieved in accordance with the invention by the characterizing features wherein the peripheral or sagittally outer boundary of the sliding surfaces of the menisci that face the femoral joint elements is higher than their central or sagittally inner boundary. This shape of the meniscal sliding surfaces represents a distinct departure from previous practice, with the effect of creating a considerably more laterally stable knee joint.

Further advantageous structural improvements include having the bearing surfaces of the tibial bearing elements found with a spherically concave curvature. The result is that the menisci are defined by spherical surfaces on all sides, which not only enables the menisci to move in the antero-posterior direction but also endows them with lateral mobility. Thus in addition to the above-mentioned increased stability of the knee-joint endoprosthesis in accordance with the invention, an increased mobility is achieved that is more like that of a natural knee joint. Because of this double-spherical configuration of the menisci, the latter become optimally positioned relative to the associated femoral joint element in every bending position of the knee.

Furthermore, the lower surface of the tibial bearing element preferably has a spherically convex curvature. Tibial implants so constructed are then set on the cortex and struck at the desired angle with a so-called impactor or hammering tool, so that due to impaction of the spongiosa the implant bed automatically acquires the necessary form-fitting shape, with no needless removal of bone.

Another disadvantage of the known systems is that the tibial bearing elements must be implanted with a particularly accurate fit in order to avoid a rocking load on the anchoring surfaces of the implant, which in any case cannot be completely eliminated when there is a single, larger-area tibial implant. The result, however, is that very often a later corrective operation would be needed, but it may be omitted or be possible only at the price of removing a relatively large piece of tibial bone. In particular, such an operation requires removal of the bearing elements, leaving behind large conical holes, with considerable deleterious effects on the bone. It should also be kept in mind that the bones of older people are no longer very stable. The process of levering the implanted bearing element out and replacing it severely weakens the bone, already suffering from the previous intervention. To resolve these problems, trial tibial bearing elements and matching trial menisci are proposed, such that at least one small projection is provided on the lower surface of the trial bearing element to anchor it in the bone. According to this proposal, the initial work on the tibia is carried out with trial bearing elements and trial menisci. The thorn or thorns provided on the lower surface of the trial bearing elements for anchoring them in the bone are intended to keep them in position and prevent lateral displacement only until the definitive position of the trial bearing element or elements has been determined, so that the definitive bearing elements can be put in place. An aiming device is used to try to position the trial bearing element optimally with respect to its longitudinal and lateral tilt as well as its height. In the process the trial bearing element may have to be removed several times in order to reshape the contact surface in the bone by means of a saw or similar instrument, until the trial bearing element can be seated in the right position, in which it makes full contact throughout the entire range of bending and extension of the knee. The bearing element for definitive implantation corresponds exactly to the trial bearing element in its dimensions. Accordingly, when the right position has been found for the trial bearing element, in relation to the associated femoral joint element, all that is needed is to replace the trial bearing element by the bearing element for definitive implantation. The bearing element for definitive implantation is provided with anchoring means that extend considerably further into the bone. However, these cause no further damage because the bearing element for definitive implantation needs to be implanted only once, in the position that was found to be optimal during the preceding tests with the trial bearing element. The anchoring thorns on the lower surface of the trial bearing element do not penetrate very far into the bone, and their effect on the bone is correspondingly slight, so that the bone is not adversely affected by multiple removal and replacement of a trial bearing element. The curvature of the lower surface of the tibial bearing elements as described above is constructed to provide additional fixation of the element at the proximal end of the tibia.

Because the tibial bearing for the menisci comprises two separate parts, the corresponding bearing surfaces can be adjusted independently of one another. This applies with respect to both their longitudinal and lateral tilt and their distance from the left and right femoral joint element, or to a single unit in which these two joint elements are combined to form a femoral "sled" with two runners. Owing to the lack of a rigid connection between the two tibial implants, moreover, there is no undesirable "rocking" of the tibial seating such as often occurs in the case of an implant constructed in one piece. Such rocking also loosens the tibial implant, with the consequence that the latter often must be replaced after a relatively short time.

The system in accordance with the invention is additionally characterized by intercompatibility between femoral joint elements, tibial bearing elements and the menisci, preferably made of polyethylene or similar material. The described system is suitable for all levels of treatment i.e., for a femoral-tibial or femoral-patellar implantation, in particular either a so-called partial or semi-prosthesis or a full prosthesis, as well as a revision prosthesis.

Another aspect of special significance is the provision of a groovelike slideway in which the trial or definitive menisci can slide over the upper surface of the trial bearing element and over the upper surface of the definitively implanted tibial bearing element. The groovelike slideway is preferably curved around the long axis of the tibia or the transverse axis of the knee. As a consequence of this "trough- or dish-like" receptacle for the menisci, the latter can be made relatively high over their full width. Accordingly, a relatively large amount of polyethylene material is available to support the femoral joint elements. The menisci are retained on the bearing surface of the tibial bearing elements by the groovelike slideway. This slideway is preferably configured as more fully disclosed in the illustrated embodiments of the invention.

The trial menisci, like the definitively implanted menisci, can be of different heights. Accordingly, differences in the distances between the tibial bearing elements and the associated femoral joint elements, depending on the degree of wear and tear, can be compensated.

The definitively implanted bearing elements, corresponding in shape to the trial bearing elements, each have on the lower surface at least one peglike or tablike, preferably sleeve-shaped anchoring element with at least one, in particular two transverse bores arranged one above the other. The said anchoring element preferably, to achieve better anchoring of the bearing element, is slanted with respect to the median axis of the latter, preferably at an angle of 5° to 20°. If two anchoring elements are disposed on the lower surface of the definitively implanted bearing element, they can preferably extend parallel to one another. It is also advantageous for the sleeve wall of the anchoring elements to be equipped with a cutting edge. It is thus inherent in the described system that menisci and bearing elements for definitive implantation are provided that correspond to the above-mentioned trial menisci and trial bearing elements.

In the region of the surface over which the meniscus slides, each trial bearing element comprises a bore to guide a bone-working tool, in particular a cylindrical gouge. By operating through this bore, the hole is formed that is to receive the anchoring element on the lower surface of the definitively implanted bearing element. In this respect, too, the trial bearing element is especially advantageous for the surgeon. The above-mentioned guide bore is preferably angled in a direction to correspond to the angle of the anchoring element on the lower surface of the definitively implanted bearing element.

The above-mentioned trough-like construction of the bearing element offers the additional advantage that the bearing element makes contact with the correspondingly shaped bone by way of its inner as well as its lower surface. In this way, the position of the tibial implant is permanently secured against rotation. Because the above-mentioned "rocking" is prevented, tensile loading of the interface due to raising of the tibial bearing element is avoided. Hence a distinct loosening tendency of the tibial bearing elements can be expected, even after prolonged use under heavy loads.

Instead of the femoral joint elements, if required a patella slide bearing can be employed.

The described system is fundamentally a truly spheroidal, unicompartmental sled prosthesis. Because the menisci, defined by corresponding polyethylene inlays, are not limited to movement in one plane, undesired eccentric loading of the menisci is also prevented. In every position to which the knee is bent, the menisci adjust optimally with respect to both the associated femoral joint element and the tibial bearing element, with no danger of slipping to the side. An especially advantageous feature is the universal compatibility of the implants, so that if the opposite compartment should later wear out, another implant can be added to form a complete joint with no need to remove well-seated tibial implant components.

Furthermore, care is preferably taken to ensure that not only the sagittal enveloping curves typical of the knee but every curvature is as close as possible to a sector of a circle. This feature is particularly significant with respect to production technology. The result is high mobility on the one hand, accompanied by equally high stability of the knee on the other.

BRIEF DESCRIPTION OF THE DRAWING

In the following, an exemplary embodiment of a system in accordance with the invention is described in detail with reference to the attached drawings, wherein

FIG. 16b shows a PE inlay for a patella spheroid according to FIG. 16a, in a view corresponding to FIG. 16a;

FIG. 19 shows a tibial trial bearing element in plan view;

FIG. 20 shows the trial bearing element according to FIG. 19 with trial meniscus in side view as indicated by the arrow II in FIG. 19;

FIG. 21 shows the trial bearing element according to FIG. 19 with trial meniscus in side view as indicated by the arrow III in FIG. 19;

FIG. 22 shows the trial bearing element according to FIG. 19 with trial menisci of different heights, in an end view;

FIG. 23 shows a tibial bearing element for definitive implantation, in plan view;

FIG. 24 shows the bearing element according to FIG. 23 with meniscus in side view as indicated by the arrow VI in FIG. 23;

FIG. 25 shows the bearing element according to FIG. 23 in side view as indicated by the arrow VII in FIG. 23;

FIG. 26 shows the tibial bearing element according to FIG. 23 with menisci of different heights, in an end view;

FIG. 27 shows a femoral sled in distal view; and

DESCRIPTION OF THE ILLUSTRATED EMBODIMENT

Figure 1:
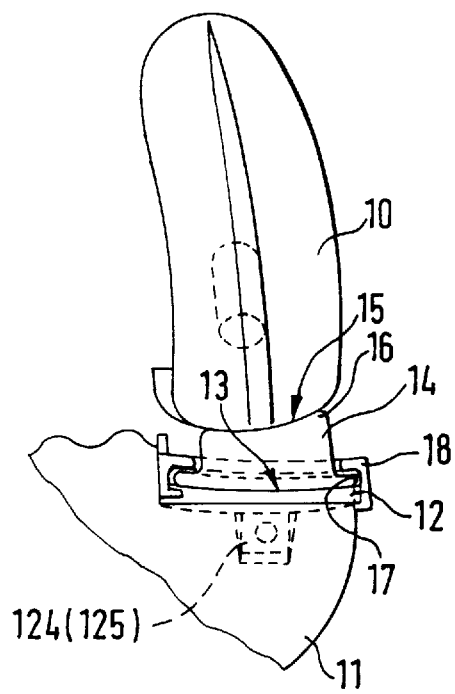
FIG. 1 shows a knee-joint hemi-endoprosthesis in front view.
Figure 2:
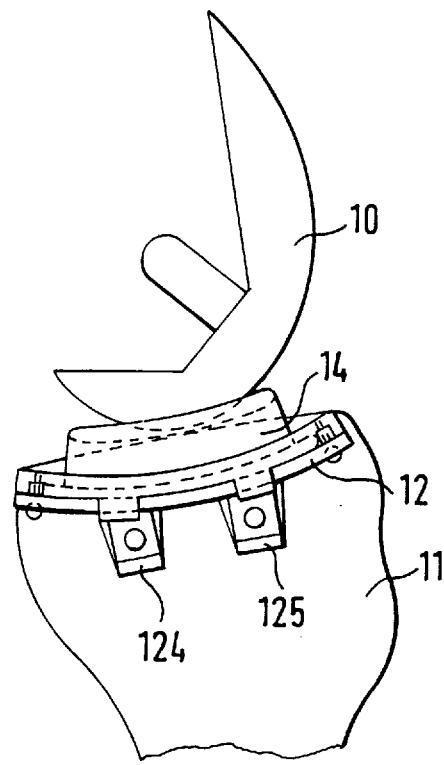
FIG. 2 is a side view of the hemi-prosthesis of FIG. 1.
Figure 3:
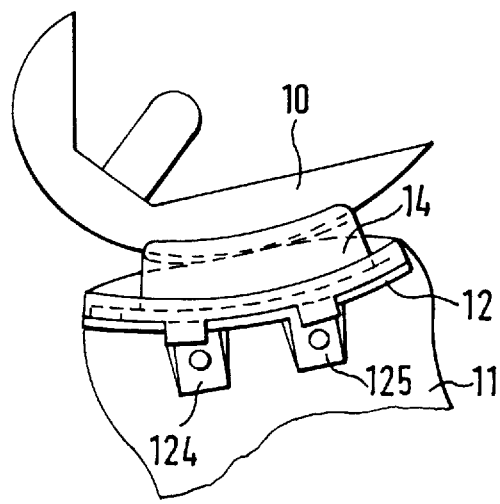
FIG. 3 shows the hemi-prosthesis according to FIG. 2 with the femoral joint element and associated meniscus in a different position relative to one another.
Figure 4:
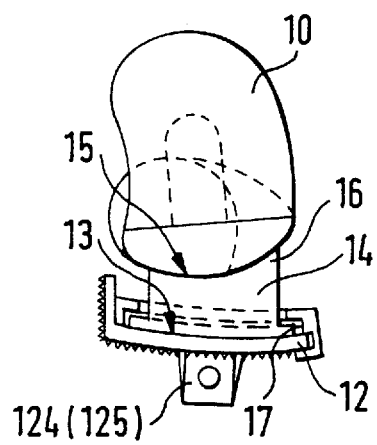
FIG. 4 is a back view of the hemi-prosthesis according to FIG. 3.
Figure 9:
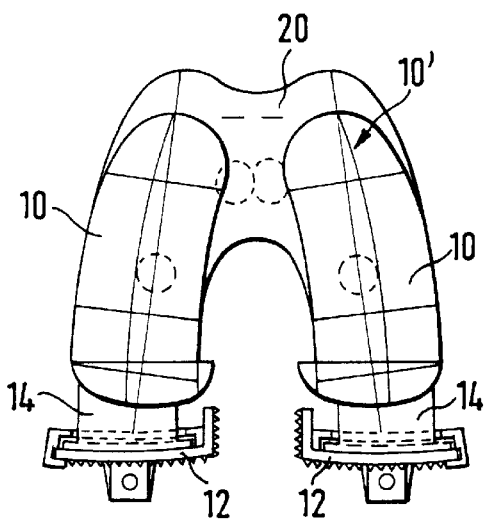
FIG. 9 shows a double-runner femoral sled with patella slide bearing in relation to two separate tibial half-implants when the knee is bent, as seen from the distal direction.
Figure 14:
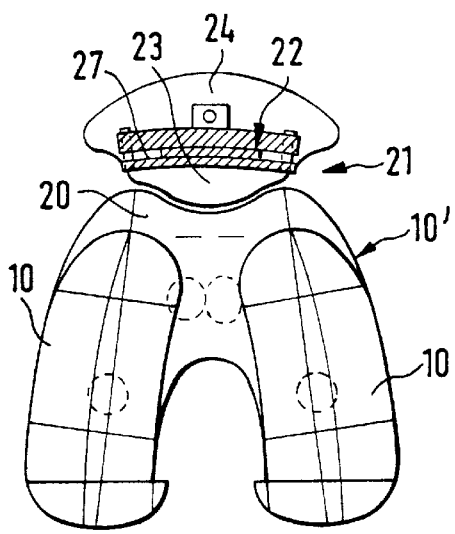
FIG. 14 shows a double-runner femoral sled with patella spheroid, in the bent state as seen from the distal direction.
Figure 15A:
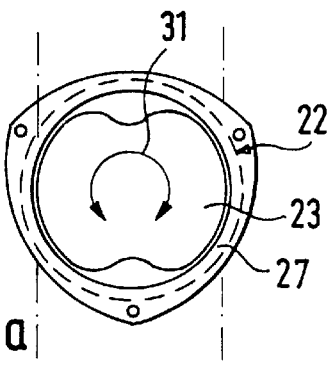
FIG. 15a shows a patella spheroid as viewed from below with knee extended.
Figure 15B:
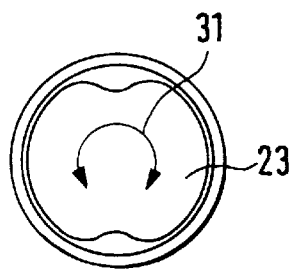
FIG. 15b shows a PE inlay for a patella spheroid according to FIG. 15a, as seen from below.
Figure 16A:
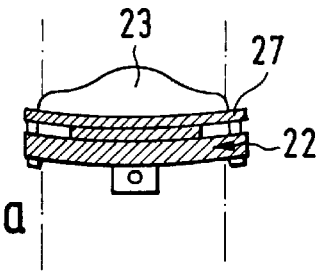
FIG. 16a shows a patella spheroid partly in cross section and partly as it appears with knee bent.
Figure 16B:

FIGS. 1 to 4 show half a knee-joint endoprosthesis in the bent position (FIGS. 1 and 2) and extended position (FIGS. 3 and 4). In these drawings, at the lower end of a femur there is disposed a joint element 10 with convexly curved joint bearing surface, whereas at the upper end of the tibia 11 is fixed or anchored a bearing element 12, the bearing surface 13 of which has a spherically concave curvature. Between the femoral joint element 10 and the tibial bearing element 12, a meniscus 14 is disposed in such a way as to be movable both laterally and in the antero-posterior direction. The upper and lower surfaces of each meniscus are sliding surfaces with curvature complementary to that of the associated joint component, i.e. the surface of the femoral joint element 10 and the bearing surface of the tibial bearing element 12, respectively. The upper sliding surface of the meniscus 14 is identified by the reference numeral 15. The meniscus 14 is made of polyethylene. The tibial bearing element 12 is anchored to the bone by sleevelike anchoring elements 124, 125, in each of which is a transverse bore. As mentioned in the list of figures, FIGS. 1 and 2 show the femoral half-sled 10 in the position it occupies when the knee is bent, whereas in FIGS. 3 and 4 it is shown in the knee-extended position. The femoral half-prosthesis shown in FIGS. 1 to 4 can subsequently, in the course of a later operation, be replaced by a complete prosthesis or revision prosthesis. In this case the left (i.e., inner) and right (i.e., outer) femoral half-sleds 10 are joined to form an integral structure. This embodiment of a femoral sled is shown in FIG. 9, in spatial relation to two separate tibial half-implants; here it is identified by the reference numeral 10'.

Figure 6:
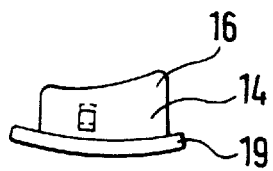
FIG. 6 shows an end face of the meniscus for the embodiment according to FIG. 1.

As can clearly be seen in FIGS. 1, 4 and 6, the peripheral or sagittally outer boundary of the sliding surface 15 of the meniscus 14, the surface that faces the femoral joint element 10, is higher than the central or sagittally inner boundary. The peripheral or sagittally outer boundary is identified by the reference numeral 16 in FIGS. 1, 4 and 6. The effect of this feature is to brace the knee joint laterally against outward displacement, and to make the joint as a whole more stable in comparison to the state of the art.

Figure 5:
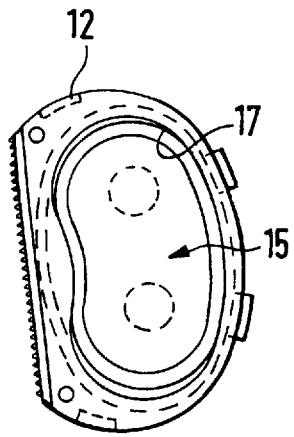
FIG. 5 is a plan view of the tibial bearing element according to FIG. 1 with its meniscus.

As has been explained briefly above, both the bearing surface of the tibial bearing elements 12 and the upper sliding surfaces 15 of the menisci 14 have a spherically concave curvature. High mobility of the knee joint in all directions is thereby achieved, with no loss of joint stability. On the contrary, the stability of the knee joint is actually further increased by these measures. Above all, the described construction endows the menisci with mobility not only in the antero-posterior direction but also to the side. In every state of bending of the knee joint, the menisci take up an optimal position with respect to both the femoral joint element 10 and the tibial bearing element 12. So that in the extreme case the meniscus will be prevented from sliding out of or being lifted away from the bearing element 12, the tibial bearing elements 12 are provided on their upper surface with a groovelike slideway 17. The groovelike slideway 17 is curved around the long axis of the tibia as shown in plan view in FIG. 5. As a result, the relative rotation of the knee joint corresponds to the natural capacity to rotate. As shown in FIG. 5, the slideway 17 runs around each meniscus 14 and holds the latter on the bearing surface 13 of the associated bearing element 12, preventing slippage in all directions. The groovelike meniscus slideway 17 in the illustrated embodiment is bounded above and at the side by guide rails 18 that can be placed on, in particular snapped onto the tibial bearing element 12. In the exemplary embodiment shown here, the guide rails 18 are part of a ring that can be snapped over the lateral edge of the associated tibial bearing element 12. Regarding the slideway arrangement see especially FIG. 5. In correspondence with the groovelike meniscus slideway 17, on the lower surface of the meniscus 14 there is a laterally projecting rim 19, which in plan view of the meniscus can be seen extending beyond the meniscus around its periphery. This peripheral rim 19 extends into the complementary groovelike meniscus slideway 17. By the cooperation between the peripheral rim 19 and the groovelike slideway 17, the meniscus 14 is held securely on the bearing element 12, such that a corresponding lateral play between the peripheral rim 19 and the groovelike slideway 17 ensures not only the customary antero-posterior mobility but also a lateral mobility of the meniscus.

It can also be seen in FIGS. 1 to 4 that the lower surface of the tibial bearing element 12 likewise has a spherically convex curvature, preferably such as to correspond to the upper surface of the bearing element. This feature makes it possible to implant the element with minimal removal of bone. The tibial bearing element is placed on the cortex and hammered in by means of an impactor so that it slants by a predetermined amount forward or back and/or to the side, during which process spongiosa impaction produces a spherically curved implant bed conforming to the lower surface of the bearing element. This implant bed can also be prepared by means of a separate impactor.

As explained at the outset, the described system provides for the use of trial tibial bearing elements with trial menisci, each trial bearing element being equipped on its lower surface with at least one, in particular two or more small thorns to anchor it in the bone. The anchoring thorns are advantageously disposed in rows on the lower surface of the trial tibial bearing element, in particular near the two sagittal long edges of the trial bearing element.

Both the trial menisci and the definitively implanted menisci 14 can be constructed in different heights. Furthermore, in practice it is also useful to have available at least three different sizes of both the trial bearing elements and the definitively implanted bearing elements.

The sliding surfaces of the bearing elements are preferably polished smooth.

By means of the anchoring thorns, which do not penetrate very deeply into the bone, a trial bearing element can be provisorily held in place without damaging the bone until the correct position or plane of the bearing element and associated meniscus relative to the associated femoral joint element has been found. In some circumstances, to achieve correct positioning it will be necessary to remove the trial bearing element several times so that the contact surface of the bone can be reshaped, and then to replace the trial bearing element, until finally the correct longitudinal and transverse inclination of the bearing element and the correct height of the meniscus have been established. Then a hole is prepared in the tibia by means of a tool, preferably a cylindrical gouge, inserted through a bore in the sliding surface of a trial meniscus and in the trial bearing element. This hole in the tibia serves to receive an anchoring element 124 or 125 disposed on the lower surface of the definitively implanted bearing element as indicated in FIGS. 1 to 4. The trial bearing element and the associated trial menisci are constructed in substantially the same way as the definitively implanted components. The trial bearing element differs from the definitively implanted bearing element essentially only in having smaller anchoring thorns on its preferably planar lower surface, rather than the anchoring elements that penetrate more deeply into the bone, on the preferably spherically convex lower surface of the definitively implanted bearing element.

Figure 7:
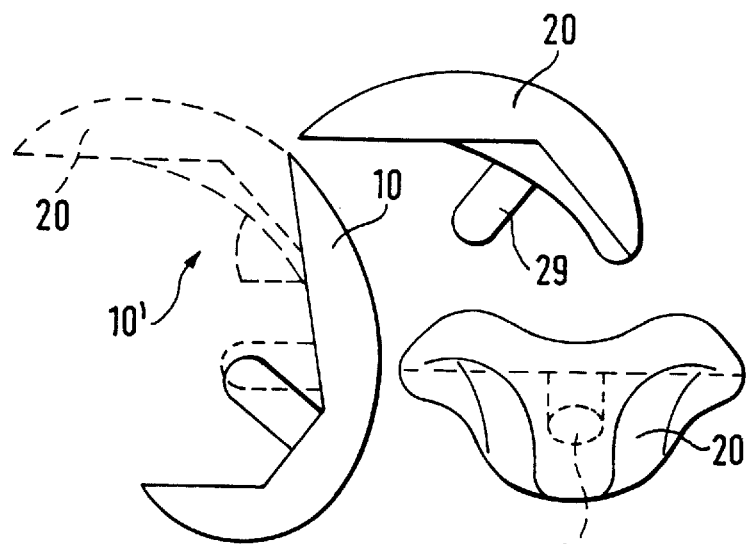
FIG. 7 shows a femoral joint part with associated patella slide bearing as seen from the side, and the patella slide bearing also as seen from the front.
Figure 8:
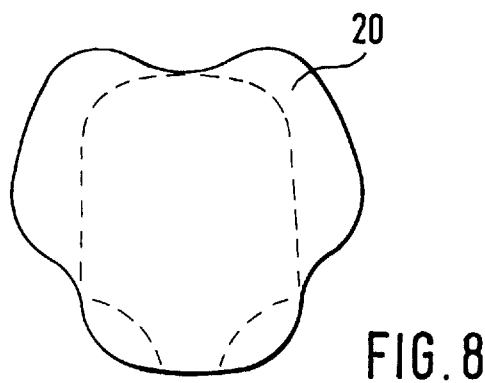
FIG. 8 shows the patella slide bearing according to FIG. 7 in plan view.

In FIG. 7 a femoral double-runner sled 10' is shown in side view. Next to the back of its proximal end there can be placed a patella slide bearing 20, seen from the side at the top of FIG. 7 and from the front at the lower right in FIG. 7. In FIG. 8 the patella slide bearing 20 is shown in plan view. Thus the described knee-joint endoprosthesis system includes a compatible femuropatellar joint prosthesis.

Figure 13:
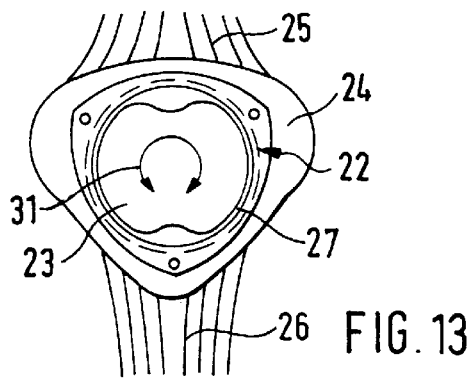
FIG. 13 shows the implanted patella spheroid according to FIGS. 11 and 12 as viewed from below with knee extended.
Figure 10:
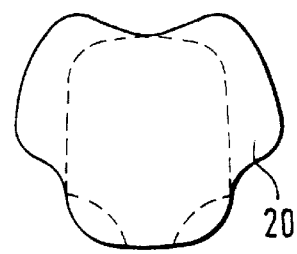
FIG. 10 shows a patella slide bearing in plan view with knee extended.
Figure 11:
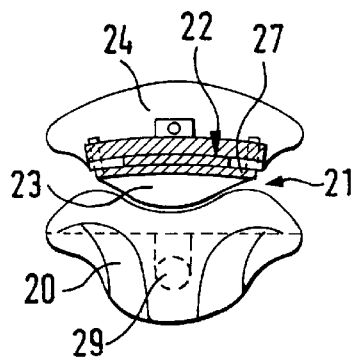
FIG. 11 shows the patella slide bearing according to FIG. 10 with associated patella spheroid as seen from the distal direction and partially in cross section, with knee bent.
Figure 12:
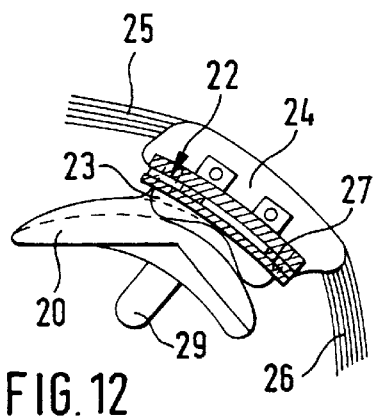
FIG. 12 shows the arrangement according to FIG. 11 in side view and partially in longitudinal section.

With reference to FIGS. 10–18b an embodiment of a patella slide-bearing prosthesis is described in greater detail, as part of the system described above. Here the femoropatellar part of the system comprises a patella slide bearing 20 that occupies the region between the two femoral half-sleds 10 (see also the relevant description with reference to FIGS. 7 and 8) and a so-called patella spheroid 21 that is placed between the femoral patella slide bearing 20 and the bony patella (kneecap) 24, in such a way as to be fixed in position with respect to the lower surface of the patella 24, i.e. the surface facing into the knee. The patella spheroid 21 itself consists of a spherical or spheroidal rotational slide bearing 22 for a supporting and sliding element in the form of a polyethylene (PE) inlay 23, by way of which the patella 24 rests against the femoral patella slide bearing 20. In this regard see especially FIGS. 11–14. In FIGS. 12 and 13 the tendons associated with the patella 24 are also shown, namely the quadriceps tendon 25 and the patellar ligament 26. The PE inlay 23 is held or secured on the spherically curved rotational slide bearing 22 by a snap-ring 27, in such a way that the required rotational sliding movement of the inlay 23 relative to the rotational slide bearing 22 is not impeded. The rotational sliding surface of the rotational slide bearing 22 is defined by a spherically curved metal plate, in particular a plate made of e.g. a titanium alloy. On the side of the plate away from the rotational sliding surface, i.e. facing the patella 24, there are provided anchoring elements for attachment to the bone, corresponding to the tibial anchoring elements 124, 125 described above.

Anchoring of the femoral patella slide bearing 20 is brought about by a femoral anchoring peg 29 (see FIGS. 7 and 12). The rotational sliding movement of the PE inlay 23 is indicated by the curved double-headed arrow 31 in FIGS. 13, 15a, 15b.

Figure 17:
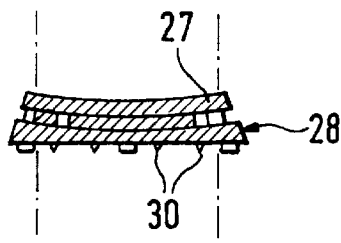
FIG. 17 shows a spherical trial rotational slide bearing with securing ring for a PE inlay, in cross section.
Figure 18A:
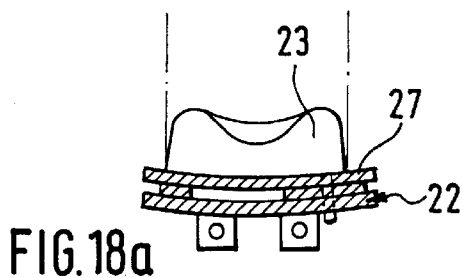
FIGS. 18a, 18b show a longitudinal section and a side view of a patella spheroid or PE inlay according to FIGS. 16a, 16b.
Figure 18B:
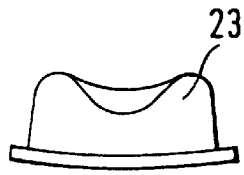

FIG. 17 shows a spherical trial rotational slide bearing 28 with snap-ring 27. This trial bearing differs from the definitively implanted rotational slide bearing 22 in that it has relatively small anchoring thorns 30, just sufficient to secure the trial bearing 28 temporarily to the patella 24. Furthermore, the contact surface facing the patella is flat, i.e. with no convex curvature such as is preferable for the definitively implanted rotational slide bearing 22. That is, the convexly curved bone-contact surface of the rotational slide bearing 22 corresponds to the anatomical shape of the residual patella 24, so that no great modification of the biomechanical lever arms is introduced.

The circular-rotation freedom of the PE inlay 23, corresponding to the double-headed arrow 31, allows a congruent fit to the femoral patella slide bearing 20 even in knee positions in which the directions in which the patella is pulled by the quadriceps and toward the tibia (by the patellar ligament) are not parallel to one another and also not parallel to the furrow in the femoral patella slide bearing 20.

The patella spheroid, in particular the spherical rotational slide bearing 22, is preferably implanted by pressing it into the residual patella 24.

The trial rotational slide bearing 28, like the unicompartmental tibial implants, is used for lateral centering and for adjustment of the tilt of the implant in the sagittal plane, and it is correspondingly provided with bores through which a cylindrical gouge can be employed to make holes for the anchoring elements of the definitively implanted patella bearing element.

Figure 28:
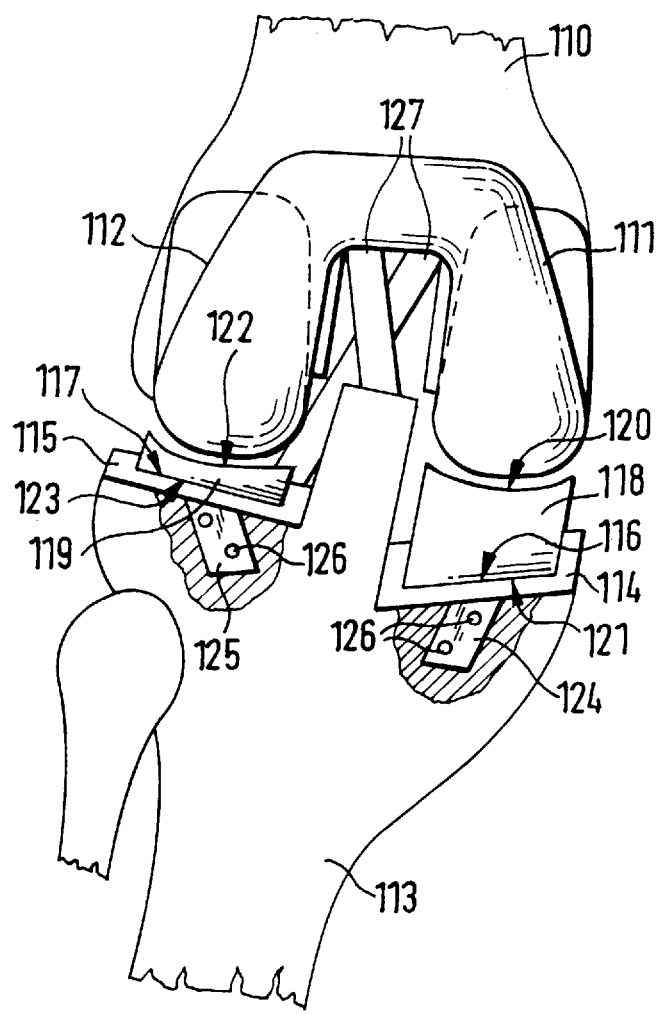
FIG. 28 shows a knee-joint endoprosthesis with femoral double-runner sled and two tibial implants positioned independently of one another, in schematic front view with knee extended.

The basic components of a knee-joint total endoprosthesis with the described system will again be described with reference to FIG. 28. As shown there, at the lower end of a femur 110 are disposed two joint elements (slide runners) 111, 112, each with a convexly curved joint bearing surface, whereas at the upper end of the tibia 113 are attached or anchored bearing elements 114, 115 with planar bearing surface 116, 117. Preferably the bearing surfaces 116, 117 are made spherically concave as described above. Between each of the femoral joint elements 111, 112 and the tibial bearing elements 114, 115 there is movably disposed a meniscus 118, 119. Each meniscus is provided on its upper and lower sides with sliding surfaces 120, 121 and 122, 123, the curvature of which is complementary to that of the associated joint bearing surface of the femoral joint element 111 or 112, or to that of the associated bearing surface of the tibial bearing element 114 or 115. Both of the menisci 118, 119 are made of polyethylene. The tibial bearing elements 114, 115 are anchored to the bone by sleevelike anchoring elements 124, 125 with one or two transverse bores 126, the anchoring sleeves 124, 125 here being tilted at an angle to the long axis of the tibia 113. The cruciate ligaments are identified in FIG. 28 by the reference numeral 127. The tibial implants of interest here and the associated system for positioning them are described in more detail with reference to FIGS. 19 to 26. With regard to FIG. 27, it should also be mentioned that whereas the so-called femoral sled shown there from the front and with the knee extended is constructed with the inner and outer joint elements integrally joined together, a separate construction is equally conceivable, in particular when at first only a half-prosthesis is required and subsequently, in the course of a later operation, a full prosthesis or revision prosthesis is implanted. In this regard see also the description of FIGS. 1–9. The complete femoral sled is identified in FIG. 27 by the reference numeral 128.

FIGS. 19–22 show a trial tibial bearing element 129 with trial meniscus 130, the basically flat lower surface of the trial bearing element 129 being provided with several anchoring thorns 131 for attachment to the bone. The anchoring thorns 131 are arranged in rows along the two longitudinal edges of the trial bearing element, as shown in FIG. 22. By means of these thorns 131, which do not penetrate very deeply into the bone, the trial bearing element can be provisorily anchored without damaging the bone, until the correct position or plane of the bearing element and associated meniscus relative to the associated femoral joint element has been found. To achieve this, in some circumstances it will be necessary to remove the trial bearing element 129 several times, in order to reshape the underlying bone, and then to replace the trial bearing element, until finally the correct longitudinal and transverse angles of the bearing element and the correct height of the meniscus have been established. Then, through a bore 132 in the sliding surface 133 of the meniscus, a hole can be or is formed in the tibia, preferably by means of a cylindrical gouge. This hole in the tibia serves to receive an anchoring element 124 in the shape of a rod, tab or sleeve disposed on the lower suface of the definitively implanted bearing element, which is shown in FIGS. 24, 25, 26 and 28.

In FIGS. 23–26 the reference numeral 134 identifies the bearing element definitively to be implanted with its meniscus 135, which matches in size and shape the trial bearing element with trial meniscus shown in FIGS. 19–22. Accordingly, both the trial bearing elements 129 and the definitively implanted tibial bearing elements 134 have on their upper surface a groovelike slideway 135 for the trial meniscus 130 or definitively implanted meniscus 136. The groovelike slideway 135, as shown in plan view in FIGS. 19 and 23, is curved about the long axis of the tibia or transverse axis of the knee. This feature makes possible a relative rotation of the knee joint corresponding to the natural capacity for rotation.

As shown in FIGS. 22 and 26, at least one of the two longitudinal side walls 137 and 138 of the groovelike slideway 135 slants outward in the direction from top to bottom, the associated longitudinal side wall of the trial meniscus 130 and the definitively implanted meniscus 136 being slanted at a complementary angle. As a result, the menisci are secured against an undesired upward displacement from the bearing element. Furthermore, the inner longitudinal side wall is somewhat higher than the outer longitudinal side wall, as is clearly shown in FIG. 26. This arrangement allows the bearing element to be better braced against the central column of bone.

As also shown in FIGS. 22 and 26, both the trial menisci 130 and the definitively implanted menisci 136 are constructed in different heights. These are indicated in FIGS. 22 and 26 by the variously high slide-bearing surfaces 120.

As discussed above, the definitively implanted bearing elements 134 corresponding to the trial bearing elements 129 each have on their lower surface at least one anchoring element 124 (in FIG. 28 also 125) in the form of a peg, tab or sleeve, with at least one transverse bore 126. A sleevelike anchoring element with transverse bore 126 offers the advantage that it is optimally incorporated by bone growth. In addition, only a minimal amount of bone substance needs to be removed during implantation, namely by means of the above-mentioned cylindrical gouge or milling cutter. As shown in FIGS. 24 to 26 and 28, the anchoring elements 124 and 125 are slanted with respect to the flat lower surface of the bearing element 134, such that the angle between the perpendicular to the surface and the long axis of the anchoring element 124 or 125 is about 5° to 20°. In the implanted state the anchoring elements preferably slant toward the long axis of the tibia, as shown schematically in FIG. 28.

Menisci for definitive implantation, corresponding to the trial menisci 130, are of course also provided, as can be seen by comparing FIG. 22 with FIG. 26. FIGS. 22 and 26 further make clear that the bearing elements 129 and 134 are each troughlike in cross section. As a result, the height of the menisci can be maximized over their entire width.

In practice it is useful to have available three different sizes of both the trial bearing elements and the definitively implanted bearing elements for insertion of the menisci. The sliding surfaces of the bearing elements are preferably polished smooth.

Because of the trough-shaped cross section of the bearing elements, it is possible to anchor the latter to the tibia in such a way that they make contact with the bone at their lower surface as well as their inner side. The bearing elements are thus permanently held fast in the bone. It is necessary merely to exchange the meniscus when required, the height of the new meniscus being chosen to allow for any change in the spatial relationships brought about in the interim by stressing and abrasion of the knee and/or the previous meniscus. The new meniscus in turn should ensure the original lateral stability and correct overall knee axis. In FIGS. 19 and 23 the sliding mobility of the meniscus within the groovelike slideway 135 is indicated by the double-headed arrow 139.

All the characteristics disclosed in the application documents are claimed as essential to the invention, to the extent that they are new to the state of the art singly or in combination.

I claim:

1. A system for producing a knee-joint endoprosthesis for attachment to the femur and the tibia of a knee, comprising:

femoral joint elements (10, 10'; 111, 112) adapted to be attached to the lower end of the femur (110) and each having an articular bearing surface with a convex curvature, separate tibial bearing elements (12; 114, 115; 134) adapted to be attached to the upper end of the tibia (11; 113) and each having a bearing surface, said tibia having a longitudinal axis, respective meniscus elements (14; 118, 119; 136) disposed between said femoral joint elements (10, 10'; 111, 112) and said tibial bearing elements (12; 114, 115; 134) and said meniscus elements having sliding surfaces (15, 120, 121, or 122, 123) formed at least on an upper side and a lower side and complementary in shape to the associated joint bearing surface of the femoral joint element (10, 10', 111, 112) and the tibial bearing element (12; 114, 115; 134), and wherein at least one of said tibial bearing elements (12; 114, 115, 134) is configured to be inclined relative to the longitudinal axis of the tibia (11; 113) and said tibial bearing elements (12; 114, 115, 134) are configured to be disposed at different levels relative to the longitudinal axis of the tibia (11; 113).

2. The system of claim 1 wherein said meniscus elements include final implanted menisci (118, 119; 136) and trial menisci (130), and wherein both said final and trial menisci are configured to be located at different levels relative to the longitudinal axis of the tibia.

3. The system of claim 2 wherein said tibial bearing element (12) includes a groove-like sliding guide (17; 135) on an upper side for receiving the trial meniscus and the finally implanted meniscus (14; 118, 119; 136) and wherein said groove-like sliding guide (17; 135) is configured to curve around a longitudinal axis of the tibia.

4. The system of claim 3 wherein said groove-like guide (135) has two longitudinal side walls (137 or 138, respectively) and at least one of said side walls slants outward from top to bottom with a mating longitudinal side wall of said trial meniscus (130) or said finally implanted meniscus (118, 119; 136), respectively, which is slanted in a complementary manner.

5. The system of claim 3 wherein said groove-like meniscus sliding guide (17) is limited upwardly and laterally by guiding bars (18) adapted to be mounted on said tibial bearing element (12) and having a bearing surface (13) with a spherical concave curvature permitting lateral play of the meniscus (14) within the groove-like sliding guide (17), and with a lateral clearance within said groove-like sliding guide (17) with the bearing surface (13) with a spherical-concave curvature.

6. The system of claim 5 wherein said guiding bars (18) of said groove-like meniscus sliding guide (17) are part of a ring-like member adapted for quick-snap action mounting over a lateral edge of the associated tibial bearing element (12).

7. The system of claim 1 wherein said sliding surfaces (15; 120; 122) of said meniscus elements (14; 118, 119; 136) includes a sagittal outer side, and said sagittal outer side includes a boundary (116) facing said femoral joint elements (10, 10', 111, 112), and configured to be located at a level higher than the level of a boundary of a sagittal inner side relative to the longitudinal axis of the tibia (11; 113).

8. The system of claim 1 wherein said bearing surface of said tibial bearing element has a spherical-concave curvature.

9. The system of claim 8 wherein each of said tibial bearing elements (12) has a lower side with a spherical-convex curvature corresponding to said bearing surface of said tibial bearing elements.

10. The system of claim 1 including tibial trial bearing elements (129) and trial menisci (130), each said tibial trial bearing element having at least one small anchoring thorn (131) on a lower side.

11. The system of claim 10 including said at least one anchoring thorn (131) disposed in the vicinity of sagittal longitudinal edges on the lower side of said tibial trial bearing elements.

12. The system of claim 11 wherein said thorns are on a planar lower side.

13. The system of claim 10 including final implant bearing elements (12; 114, 115; 134) corresponding to said trial bearing elements (129) without having an anchoring thorn, and each said final implant bearing element has on a lower side at least one clip-like anchoring element (124, 125).

14. The system of claim 13 wherein said final implanting bearing element includes a flat lower surface, and said anchoring element (124, 125) extends at an inclination relative to the flat lower surface of said bearing element (114, 115; 134), said angle between the surface and a longitudinal axis of said anchoring element (124, 125) having a value from substantially 5° to 20°.

15. The system of claim 14 including a plurality of anchoring elements (124, 125) with different anchoring elements slanted to different degrees with respect to the flat lower surface of said bearing element (114, 115; 134).

16. The system of claim 10 wherein each said trial bearing element includes a meniscus sliding surface (133) which includes a bore (132) for guiding a bone-working tool including a cylindrical gouge.

17. The system of claim 10 including final menisci (14; 118, 119; 136) corresponding to said trial menisci.

18. The system of claim 1 wherein said femoral joint elements are part of an integral femur sled (10') or two half-sleds (10 or 111, 112) separated from one another.

19. The system of claim 18 including a patella sliding bearing (20) coupled to the femur sled (10') or the said two half-sleds (10 or 111, 112).

20. The system of claim 19 wherein the patella sliding bearing (20) includes a patella spheroid (21) adapted to be disposed between the patella (24) and a sliding and support element on the patella slide bearing (20), and having a pivot sliding bearing (22) including anchoring elements for anchoring it to the patella (24).

21. The system of claim 20 including a spherical trial pivot slide bearing (28) and having a small anchoring thorn (30) on one side, said anchoring thorn being just sufficient to temporarily secure said trial bearing (28) to the patella (24).

* * * * *